United States Patent [19]

Fisher et al.

[11] Patent Number: 5,008,250

[45] Date of Patent: Apr. 16, 1991

[54] NEW AVERMECTINS WITH A CLEAVED FURAN RING AND AN 8A HYDROXY GROUP

[75] Inventors: Michael H. Fisher, Ringoes; Matthew J. Wyvratt, Mountainside; Helmut Mrozik, Matawan, all of N.J.

[73] Assignee: Merck & Co., Inc., Rahway, N.J.

[21] Appl. No.: 198,271

[22] Filed: May 25, 1988

[51] Int. Cl.$^5$ .................. A61K 31/35; A61K 31/70; C07H 17/08

[52] U.S. Cl. ................................ 514/30; 514/450; 536/7.1; 549/264; 549/265; 71/88

[58] Field of Search ................ 536/7.1; 549/264, 265; 514/30, 450; 71/88

[56] References Cited

U.S. PATENT DOCUMENTS 4,301,164 11/1981 Ohno et al. .................... 549/60

FOREIGN PATENT DOCUMENTS

0170006A2 3/1985 European Pat. Off. .
0205251 12/1986 European Pat. Off. ............ 549/264
0139079 8/1982 Japan .................... 549/264

OTHER PUBLICATIONS

D. L. Bull, et al., J. Agric. Food Chem., 1984, 32, 94–102.

Primary Examiner—John W. Rollins
Assistant Examiner—Elli Peselev
Attorney, Agent, or Firm—David L. Rose; Hesna J. Pfeiffer

[57] ABSTRACT

There are disclosed novel avermectin compounds having a cleaved furan ring and a hydroxy group in the 8a position. Processes for preparing these novel compounds are also disclosed. These compounds have utility as anti-parasitic agents and as insecticides against agricultural pests.

14 Claims, No Drawings

NEW AVERMECTINS WITH A CLEAVED FURAN RING AND AN 8A HYDROXY GROUP

BACKGROUND OF THE INVENTION

The term avermectin (previously referred to as C-076) is used to describe a series of compounds isolated from the fermentation broth of an avermectin producing strain of Streptomyces avermitilis and derivatives thereof. The morphological characteristics of the culture are completely described in U.S. Pat. No. 4,310,519. The avermectin compounds are a series of macrolides, each of which is substituted thereon at the 13-position with a 4'-(α-L-oleandrosyl)-α-L-oleandrose group. The avermectin compounds and the instant derivatives thereof have a very high degree of anthelmintic, insecticidal and anti-parasitic activity.

Also included in the prior art are certain synthetically modified avermectins such as 22,23-dihydro avermectin B1a/B1b, also known as ivermectin.

The avermectin series of compounds, which are isolated from a fermentation broth, have the following structure:

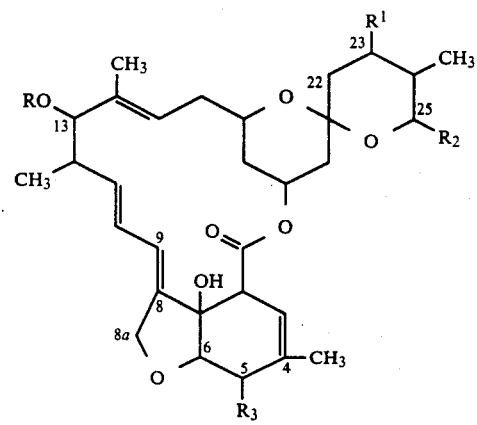

wherein R is the 4'-(α-L-oleandrosyl)-α-L-oleandrose group of the structure:

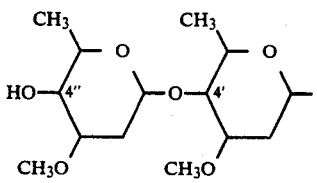

and wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'-(α-L-oleandrosyl)-α-L-oleandrose):

|  | 22,23 | $R_1$ | $R_2$ | $R_3$ |
|---|---|---|---|---|
| A1a | Double Bond | — | sec-butyl | —OCH$_3$ |
| A1b | Double Bond | — | iso-propyl | —OCH$_3$ |
| A2a | Single Bond | —OH | sec-butyl | —OCH$_3$ |
| A2b | Single Bond | —OH | iso-propyl | —OCH$_3$ |
| B1a | Double Bond | — | sec-butyl | —OH |
| B1b | Double Bond | — | iso-propyl | —OH |
| B2a | Single Bond | —OH | sec-butyl | —OH |
| B2b | Single Bond | —OH | iso-butyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The milbemycin compounds, which have a methyl or ethyl group at the 25-position and lack the 13-disaccharide group are also starting materials for the instant compounds. They are disclosed in U.S. Pat. No. 3,950,360.

SUMMARY OF THE INVENTION

The instant invention is concerned with certain derivatives of avermectin having a cleaved furan ring and a hydroxy group in the 8a position. Thus, it is an object of this invention to describe such avermectin derivatives. A further object is to describe processes for the preparation of such compounds. A still further object is to describe the uses of such compounds as anthelmintic agents. An additional object is to describe the uses of such compounds as insecticidal agents for the treatment of household and agricultural insect pests. Still further objects will become apparent from the reading of the following description.

DESCRIPTION OF THE INVENTION

The compounds of the instant invention have the following formula:

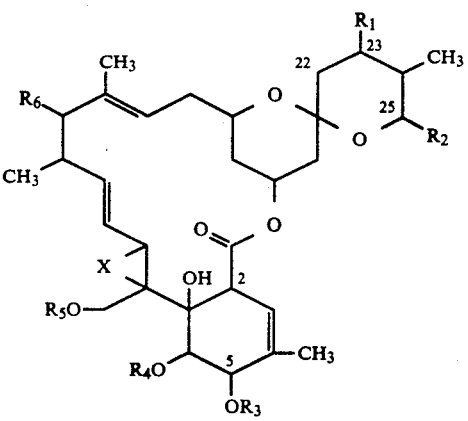

wherein the broken line at the 22,23-position indicates a single or double bond;

$R_1$ is H or hydroxy; the hydroxy being present only when said broken line indicates a single bond;

$R_2$ is methyl, ethyl, iso-propyl or sec-butyl;

$R_3$ is hydrogen, methyl or acyl;

$R_4$ and $R_5$ are hydrogen or acyl;

X is oxygen or a double bond;

$R_6$ is hydrogen, hydroxy,

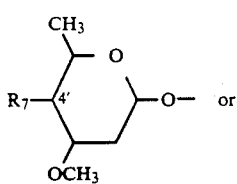

or

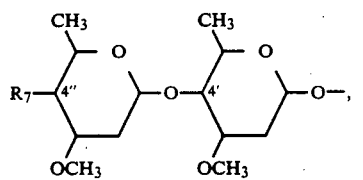

wherein $R_7$ is hydroxy, $-NR_8R_9$, wherein $R_8$ and $R_9$ are independently hydrogen, loweralkyl, loweralkanoyl, loweralkyl sulfonyl or substituted benzenesulfonyl, wherein the substituent is halogen or $R_{10}COO-$, wherein $R_{10}$ is a loweralkyl, phenyl or loweralkyl substituted phenyl.

In the instant description, the term "loweralkyl" is intended to include those alkyl groups containing from 1 to 6 carbon atoms in either a straight or branched chain. Exemplary of such alkyl groups are methyl, ethyl, propyl, isopropyl, butyl, sec-butyl, pentyl, hexyl and the like.

The term "loweralkanoyl" is intended to include those alkanoyl groups of from 2 to 6 carbon atoms of either a straight or branched chain. Such groups are exemplified by acetyl, propionyl, butyryl, pentanoyl, hexanoyl and the like.

The term "halogen" is intended to include the halogen atoms, fluorine, chlorine, bromine and iodine.

The term "loweralkyl substituted phenyl" is intended to include those substituted phenyls having alkyl groups containing from 1-4 carbon atoms of either straight or branched chain. Such groups are exemplified by tolyl, phenethyl, phenbutyl, 3-phenyl-2-isobutyl and the like.

Examples of preferred compounds of this invention are as follows:

6,8a-Deepoxy-6,8a-dihydroxyavermectin B1a and/or B1b 6,8a-Deepoxy-6,8a-dihydroxy-22,23-dihydroxyavermectin B1a/B1b 6,8a-Deepoxy-6,8a-dihydroxyavermectin B2a/B2b 6,8a-Deepoxy-6,8-dihdroxylavermectin A1a/A1b 6,8a-Deepoxy-6,8a-dihydroxyavermectin B1a/B1b-monosaccharide 6,8a-Dihydroxy-22,23-dihydroavermectin B1a/B1b aglycone 6,8a-Deepoxy-6,8a-dihydroxy-13-deoxy-22,23-dihydroavermectin B1a aglycone 6,8a-Deepoxy-6,8a-dihydroxy-13-deoxy-22,23-dihydroavermectin B1b aglycone 6,8a-Deepoxy-6,8a-dihydroxymilbemycin $\alpha_2$ 4''-Methylamino-4''-deoxy-6,8a-deepoxy-6,8a-dihydroxy22,23-dihydroavermectin B1a/B1b 4'',5,6,8a-Tetra-O-acetyl-6,8a-deepoxy-6,8a-dihydroxyavermectin B1/B1b 6,8a-Deepoxy-6,8a-dihydroxy-22,23-dihydroavermectin B1a/B1b-8,9-oxide The "b" compounds, those with a 25-isopropyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to "the B1 or B2 compounds" or by separating the "a" compound from the "b" compound by a slash (/) such as B1a/B1b, B2b and the like.

The 8a-hydroxyavermectin B1 compound has been identified as a soil metabolite of avermectin B1 (Bull et al., J. of Agricultural and Food Chemistry, 32, 94 (1984). The 8a-oxo-avermectin starting material of the present invention is described in U.S. Pat. No. 4,547,491 and can be prepared by treating an avermectin protected at the 4'', 5 and 23 (if necessary) positions with pyridinium dichromate (PDC) in N,N-dimethylformamide. The produce can then be deprotected and reduced with sodium borohydride to yield the cleaved furan ring product [Scheme I]. Preferably, the cleaved furan ring 8a-hydroxyavermectin derivative can be prepared by treating an avermectin protected in the 5 position and in an organic solvent with tert-butylperoxybenzoate in the presence of copper (I) chloride, hydrolysis of the 8a-acyl function followed by a deprotection reaction at the 5 position. The 8a-hydroxy derivative is in equilibrium with its open aldehyde form. The aldehyde form of the hydroxylated furan ring can be reduced by treatment with $CeCl_3.7H_2O$ in ethanol and sodium borohydride [Scheme II]. These reactions are illustrated by the following schematics:

SCHEME 1
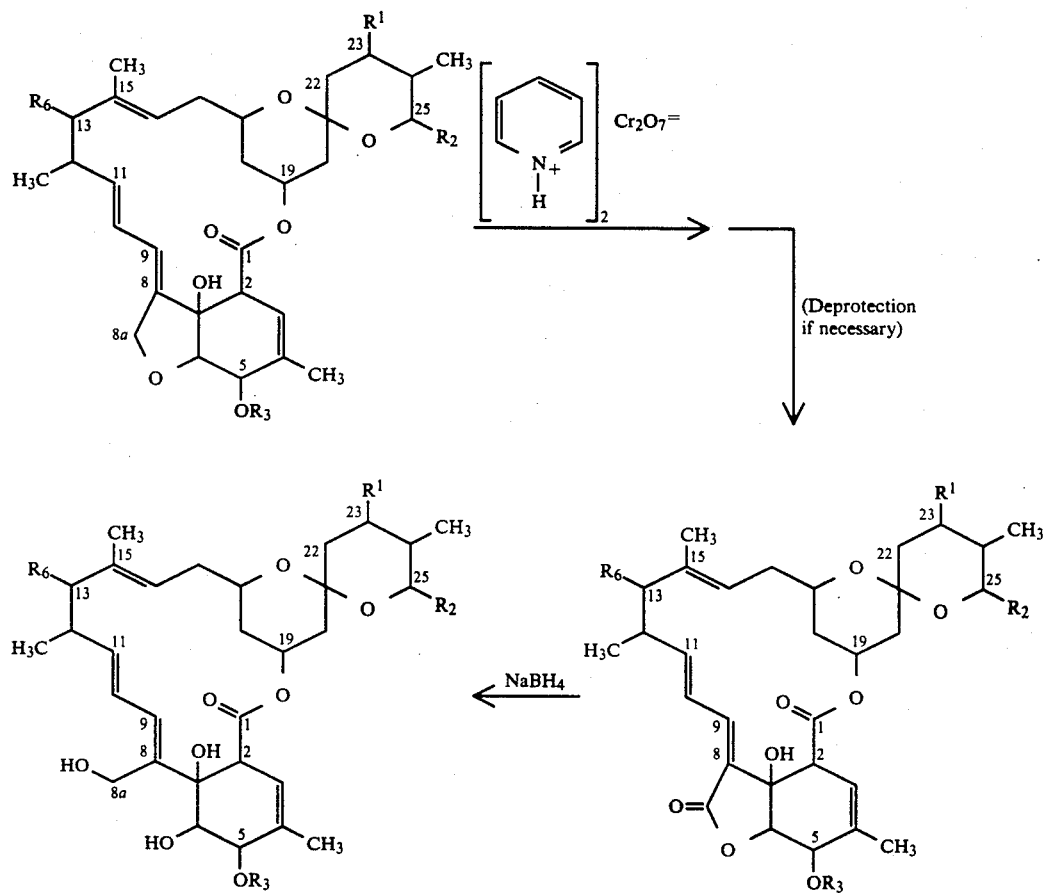
SCHEME II
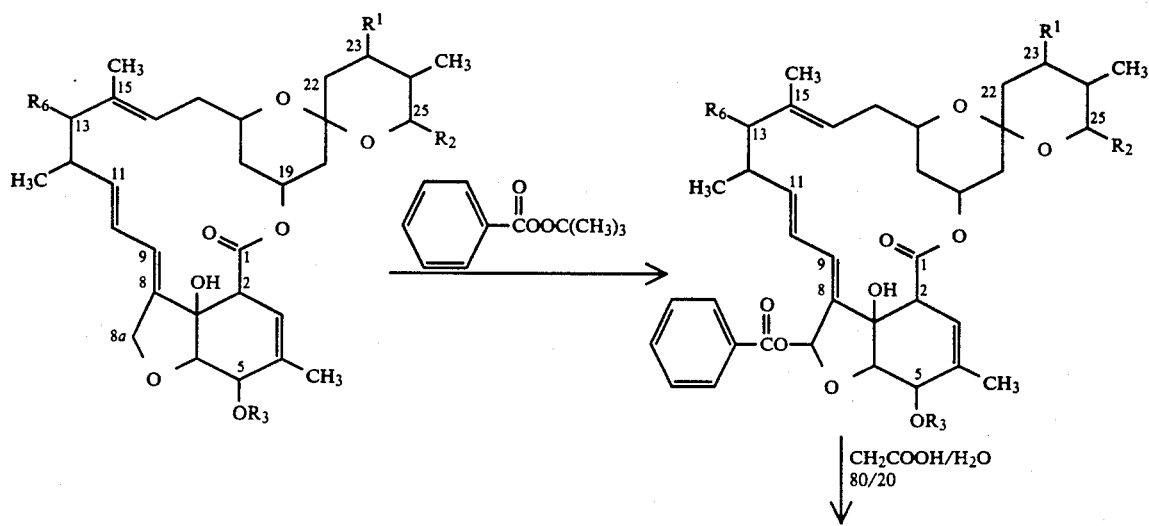

-continued
SCHEME II

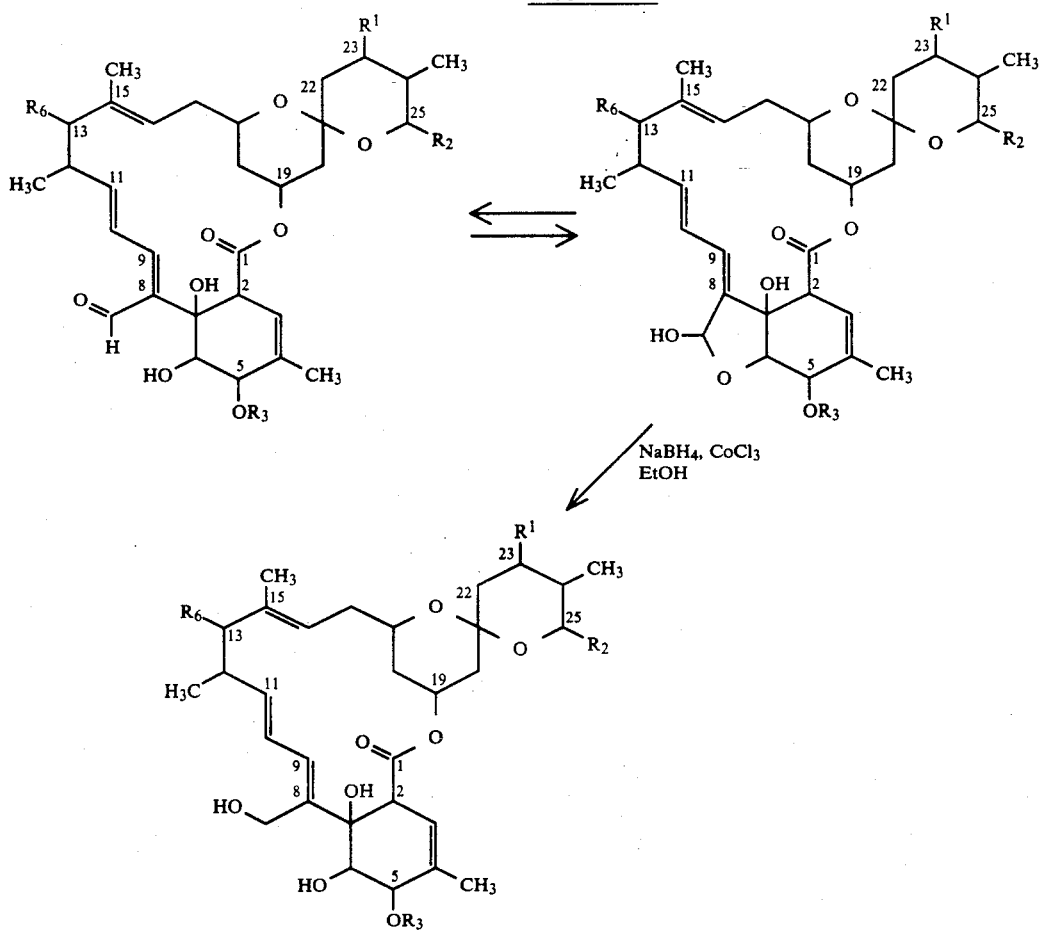

DISCUSSION OF UTILITY

The novel compounds of this invention have parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and oftentimes serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxcyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while still others such as Dictyocaulus are found in the lungs. Still others parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The cleaved furan ring compounds of this invention have activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important general of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as two-spotted spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by administering about 0.001 to 10 mg of drug per kg of animal body weight, such total dose being given at one time or in divided doses over a relatively short period of time such as 1-5 days. With the preferred compounds of the invention, control of such parasites is obtained in animals by administering from about 0.025 to 1 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. An inert carrier is one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant processes, from the fermentation broth, the various avermectin compounds will be found to have been prepared in unequal amounts. In particular an "a" series compound will be prepared in a higher proportion than the corresponding "b" series compound.

The "b" compounds, those with a 25-isopropyl group, need not be separated from the corresponding "a" compound with a 25-sec-butyl group and as such the compounds are generally isolated as mixtures of the two compounds. Thus, references in the instant application to "a" compounds such as B1a, A1a and the like, are intended to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b, and the like.

PREPARATION OF STARTING MATERIALS

The ultimate starting materials for the compounds of this invention are the avermectin and milbemycin fermentation products defined above. Thus it is apparent that additional reactions are required to prepare many of the starting materials for the instant compounds. Specifically, reactions are carried out at the 5, 4", 4', 13, 22, and 23 positions. It is generally preferred to prepare whatever substituents are required at these positions before carrying out the reactions to cleave the furan ring. Such a procedure generally avoids undesirable side reactions. This technique is not required, however, and if desired, other sequences may be used. In addition, it is often necessary to protect certain reactive hydroxy groups where reaction with the above reagents is not desired. With the appropriate positions protected, the above reactions may be carried out without affecting the remainder of the molecule. Subsequent to any of the above described reactions the protecting group may be removed and the unprotected product isolated. The protecting group employed is ideally one which may be readily synthesized, and may be readily removed without affecting any other functions of the molecule. It is noted that certain instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example is the t-butyldiemthylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at 0° to 25° C. For the 5-position hydroxy group the reaction is complete in from ½ to 3 hours at from 0° C. to room temperature. This reaction is selective to the 5 position under the conditions above described and very little silylation is observed at other hydroxy groups. Alternatively, a 5, 4", 23-tri(phenoxyacetyl) derivative can be prepared. Basic hydrolysis will leave the highly hindered 23-O-substituent but will hydrolyze the 5-and 4"-O-phenoxy acetyl groups leaving them available for reaction. The 5-position may be selectively protected as described above with tert-butyldimethylsilyl, and the 4"-hydroxy group may be reacted.

The silyl group may be removed after the other contemplated reactions have been carried out. The silyl group or groups are removed by stirring the silyl compound in methanol with a catalytic amount of an acid, preferably a sulfonic acid such as p-toluenesulfonic acid. The reaction is complete in about 1 to 12 hours at for 0° to 50° C. Alternatively, the silyl group may be removed by treatment with HF-pyridine complex in tetrahydrofuran and pyridine. The reaction is complete in about 12 hours to 5 days at room temperature.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the 1-series of compounds. Thus in the "1" series of compounds it is necessary to reduce the 22,23 double bond while not affecting the remaining four unsaturations or any other functional group present on the molecule in order to selectively prepare the 22,23-dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

$$[(Ph_3P)_3RhZ)]$$

wherein

Ph is phenyl and Z is halogen. The reduction procedure is completely described in U.S. Pat. No. 4,199,569 to Chabala et al.

Certain of the avermectin starting materials for the compounds of this invention require the removal of both of the α-L-oleandrosyl moieties (described in U.S. Pat. No. 4,206,205 to Mrozik et al.). The selective acylation of the susceptible hydroxy groups is described in U.S. Pat. No. 4,201,861 to Mrozik et al.

The reaction conditions which are generally applicable to the preparation of the aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 1 to 10% by volume. The reaction mixture is generally stirred at about 20°–40° C., preferably at room temperature, for from 6 to 24 hours. The products are isolated, and mixtures are separated by techniques such as column, thin layer, preparative and high pressure liquid chromatography, and other known techniques.

The acids which may be employed in the above process include mineral acids and organic acids such as sulfuric, hydrohalic, phosphoric, trifluoroacetic, trifluoromethane sulfonic and the like. The hydrohalic acids are preferably hydrochloric or hydrobromic. The preferred acid in the above process is sulfuric acid.

A further procedure for the preparation of the aglycone of the avermectin compounds or of the hydrogenated avermectin compounds utilizes a different solvent system. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The B1 and 22,23-dihydro B1 compounds have 2 available hydroxy groups: at the 4"-and the 5-positions. However, the two hydroxy groups have different reactivities. The 5-hydroxy group can be protected specifically by the preparation of the 5-O-tert-butyldimethylsilyl or other trisubstituted silyl derivative as described by Mrozik et al. in Tetrahedron Letters 24: 5333–5336 (1983).

The following examples are provided in order to more fully describe the present invention and are not to be construed as limitative of the invention.

The substituted avermectin derivatives prepared in the following examples are generally isolated as solids. They are characterized analytically using techniques such as mass spectrometry, nuclear magnetic resonance, and the like. The compounds are not generally characterized by sharp melting point; however, the chromatographic and analytical methods employed indicate that the compounds are of suitable purity.

In the following examples, the various starting materials therefore are avermectin compounds or derivatives of avermectin compounds. The avermectin compounds and the preparation and isolation thereof from fermentation broths are described in U.S. Pat. No. 4,310,519. The selective 22,23-dihydro derivatives of avermectin compounds are described in U.S. Pat. No. 4,199,569. The aglycone and monosaccharide derivatives of avermectin compounds are described in U.S. Pat. No. 4,206,205. The amino derivatives of avermectin compounds are described in U.S. Pat. No. 4,426,663. The milbemycins compound are described in U.S. Pat. Nos. 3,950,360, 4,171,314 and 4,173,571.

EXAMPLE 1

8a-Hydroxyavermectin B1a/B1b

To a solution of 710 mg of anhydrous 5-O-(tert-butyldimethylsilyl)avermectin $B_{1a}/B_{1b}$ in 10 ml of dry benzene, 1 mg of copper (I) chloride and 0.162 ml of tert-butyl peroxybenzoate was added under an inert atmosphere (nitrogen). The reaction mixture was then placed in a oil bath which was preheated to 95° C. The mixture was stirred at reflux for 12 hours and then added to a 5% solution of sodium bicarbonate. The layers were separated and the organic phase back-washed with brine. The organic solution was then concentrated to given a crude mixture which was desilyated and debenzolyzed in 40 ml of 80/20 acetic acid/water by stirring at room temperature for 24 hours. The reaction mixture was concentrated under reduced pressure and the residue dissolved in ethyl acetate. This solution was washed with 5% sodium bicarbonate solution and brine. The organic solution was dried over anhydrous sodium sulfate and then concentrated to give 578 mg of crude product. This material was chromatographed on silica gel (2/1 ethyl acetate/methylene chloride) to afford 170 mg of 8a-hydroxyavermectin $B_{1a}/B_{1b}$. $^1$H NMR and $^{13}$C NMR spectra (CDCl$_3$) indicate approximately a 1:3 mixture of the 8a-hydroxy derivative and its aldehydic isomer, respectively [Bull et al., Journal of Agricultural and Food Chemistry, 32, 94 (1984)]. This product can be further purified and the $B_{1a}$ and $B_{1b}$ components separated on a Whatman reverse phase column under the following conditions: Whatman Partisil M-20 10/50 ODS3 column; 68/32 acetonitrile/water; 11 ml/minutes; 254 nm; ambient temperature. Purified 8a-hydroxyavermectin $B_{1a}$ (92 mg) and 8a-hydroxyavermectin $B_{1b}$ (7.5 mg) were obtained.

EXAMPLE 2

6,8a-Deepoxy-6,8a-dihydroxyavermectin B1a

A solution of 8a-hydroxyavermectin $B_{1a}$ (25.3 mg) and CeCl$_3$.7H$_2$O (12.2 mg) in 1.5 ml of ethanol at 5° C. was treated with a solution of sodium borohydride (1.6 mg in 0.16 ml of ethanol) and the resulting mixture stirred for 1.5 hours at −5° C. The reaction mixture was distributed between ethyl acetate and 5% sodium bicarbonate solution and the layers separated. The aqueous phase was further extracted with ethyl acetate (2×10 ml). The combined organic layers were treated with brine and then dried over anhydrous magnesium sulfate. The solution was concentrated to give 25.6 mg of crude product. This material was purified by preparative TLC on silica gel (3% methanol in ethyl acetate) to afford 24.3 mg of pure product. NMR, UV and mass spectra are consistent with the structure, 6,8a-deepoxy-6,8a-dihydroxyavermectin $B_{1a}$.

EXAMPLE 3

6,8a-Deepoxy-6,8a-dihydroxyavermectin B1b

A solution of sodium borohydride (1.2 mg) in 0.15 ml of ethanol is added to a cold (−5° C.) solution of 8a-hydroxyavermectin $B_{1b}$ (5 mg) and CeCl$_3$.7H$_2$O (2.2 mg) in 0.5 ml of ethanol. The reaction mixture is stirred for 1.5 hours at −5° C. and then partitioned between ethyl acetate and 5% sodium bicarbonate solution. The layers are separated and the aqueous layer further extracted with ethyl acetate. The combined organic extracts are back-washed with brine and then dried over anhydrous magnesium sulfate. Concentration affords the crude product which when chromatographed on silica gel would afford 6,8a-deepoxy-6,8a-dihydroxyavermectin $B_{1b}$.

EXAMPLE 4

8a-Oxo-avermectin B1a/B1b

Anhydrous 4",5-di-O-(tert-butyldimethylsilyl)avermectin $B_{1a}/B_{1b}$ (0.5 g) and pyridinium dichromate [PDC] (1.2 g) in 17 ml of dry dimethylformamide (DMF) was stirred at room temperature under nitrogen for 3 days. The reaction mixture was then added to 125 ml of ethyl acetate and 100 ml of water. The layers were separated and the aqueous phase further extracted with ethyl acetate. The combined organic layers were back-washed with water (2×50 ml) and brine (50 ml) and then dried over anhydrous sodium sulfate. This solution was passed through a short silica gel column (60 ml) and the eluant concentrated to give 0.293 g of crude product. This material was chromatographed on silica gel (5/1 hexanes/ethyl acetate) to give 41.5 mg of 4",5-di-O-(tert-butyl-dimethylsilyl)-8a-oxo-avermectin $B_{1a}/B_{1b}$.

To 41 mg of 4",5-di-O-(tert-butyldimethylsilyl)-8a-oxo-avermectin $B_{1a}/B_{1b}$ in a polypropylene vial, 1 ml of a stock solution of HF-pyridine [prepared in a polypropylene vial by diluting 2 ml of commercial (HF)-pyridine (Aldrich) with 14 ml of dry tetrahydrofuran and 4 ml of dry pyridine] was added and the resulting reaction mixture permitted to stir under nitrogen for 2 days. The mixture was added to an ice-cooled aqueous solution of sodium bicarbonate with stirring and then repeatedly extracted with ethyl acetate. The combined organic layers were back-washed with 0.5N hydrochloric acid, water, saturated sodium bicarbonate solution and brine. The solution was dried over anhydrous sodium sulfate and concentrated to give 37 mg of crude product which was purified by preparative TLC on silica gel (2/1 methylene chloride/ethyl acetate) to afford 27 mg of pure 8a-oxo-avermectin $B_{1a}/B_{1b}$.

EXAMPLE 5

6,8a-Deepoxy-6,8a-dihydroxyavermectin B1a/B1b

To a solution of 15.7 mg of 8a-oxo-avermectin $B_{1a}/B_{1b}$ in 0.5 ml of anhydrous methanol, 6.7 mg of sodium borohydride was added. The reaction mixture was stirred under nitrogen for 30 minutes at which point TLC indicated the absence of starting material. Acetone (0.5 ml) was added to quench excess sodium borohydride. The reaction mixture was stirred for 5 minutes and then partitioned between ethyl acetate (15 ml) and 1M hydrochloric acid (20 ml). The organic layer was then washed with water, 5% sodium bicarbonate solution and brine. The solution was dried over anhydrous sodium sulfate and evaporated to give 14 mg of crude product. This material was purified by preparative TLC on silica gel (3% methanol in 3/1 ethyl acetate/hexanes) to afford 6.2 mg of 6,8a-deepoxy-6,8a-dihydroxyavermectin $B_{1a}/B_{1b}$ which was identical in all respect to the materials produced in Examples 2 and 3.

EXAMPLE 6

8a-Hydroxy-22,23-dihydroavermectin B1a/B1b

Tert-butyl peroxybenzoate (0.82 ml) is added to a solution of 350 mg of anhydrous 5-O-(tert-butyl-dimethylsilyl)-22,23-dihydroavermectin $B_{1a}/B_{1b}$ and 0.5 mg of copper (I) chloride in 5 ml of anhydrous benzene under nitrogen. The reaction mixture is placed in a preheated oil bath at 95° C. and the mixture stirred at reflux for 12 hours. The reaction is quenched in 5% sodium bicarbonate solution and diluted with ethyl acetate. The layers are separated and the organic phase back-washed with brine and then concentrated under reduced pressure. The residue is treated with 20 ml of 80/20 acetic acid/water and stirred at room temperature for 24 hours. The reaction mixture is evaporated and the residue dissolved in ethyl acetate. This solution is washed with 5% sodium bicarbonate solution and brine. The mixture is dried over anhydrous sodium sulfate and concentrated to afford crude product which is purified by preparative TLC on silica gel followed by preparative HPLC on a reverse phase column to give pure 8a-hydroxy-22,23-dihydroavermectin $B_{1a}/B_{1b}$ as an equilibrium mixture of hemiacetal and aldehyde.

EXAMPLE 7

6,8a-Deepoxy-6,8a-dihydroxy-22,23-dihydroavermectin B1a/B1b

To a solution of 8a-hydroxy-22,23-dihydroavermectin $B_{1a}/B_{1b}$ (50 mg) and $CeCl_3.7H_2O$ (24 mg) in 3 ml of ethanol at $-5°$ C., a solution of sodium borohydride (3.5 mg in 0.4 ml of ethanol) is added. The reaction mixture is stirred at $-5°$ C. for 1.5 hours and then poured into a mixture of ethyl acetate and 5% sodium bicarbonate solution. The layers are separated and the aqueous phase further extracted with ethyl acetate. The combined organic extracts are backwashed with brine and dried over anhydrous magnesium sulfate. Evaporation of this solution affords crude product which upon purification via preparative TLC gives 6,8a-deepoxy-6,8a-dihydroxy-22,23-dihydroavermectin $B_{1a}/B_{1b}$.

EXAMPLE 8

8a-Hydroxyavermectin B2a/B2b

A solution of 540 mg of dry 5-O-(tert-butyl-dimethylsilyl)avermectin $B_{2a}/_{2b}$ and 2 mg of copper (I) chloride in 7.5 ml of dry benzene is treated with 0.13 ml of tert-butyl peroxybenzoate under an atmosphere of nitrogen. The reaction mixture is placed in a preheated oil bath at 95° C. and the mixture stirred for 12 hours at reflux. The reaction mixture is poured into ethyl acetate/5% sodium bicarbonate solution and the layers separated. The organic layer is back-washed with brine and then concentrated, the residue is dissolve in 30 ml of 80/20 acetic acid/water and stirred at room temperature for 24 hours. The reaction mixture is concentrated and redissolved in ethyl acetate. This solution is washed with 5% sodium bicarbonate solution and brine. The organic solution is dried over anhydrous sodium sulfate and then concentrated to give crude product. This material is purified first by preparative TLC on silica gel and then by preparative HPLC on a reversephase column to give 8a-hydroxyavermectin $B_{2a}/B_{2b}$ (hemiacetal/aldehyde mixture).

EXAMPLE 9

6,8a-Deepoxy-6,8a-dihydroxyavermectin B2a/B2b

To a solution of 8a-hydroxyavermectin $B_{2a}/B_{2b}$ (26 mg) and $CeCl_3.7H_2O$ (12 mg) in 1.5 ml of ethanol at $-5°$ C., a solution of sodium borohydride (1.7 mg in 0.2 ml of ethanol) is added and the resulting mixture stirred for 1.5 hours at $-5°$ C. The reaction mixture is then distributed between ethyl acetate and 5% sodium bicarbonate solution. The layers are separated and the aqueous layer further extracted with ethyl acetate. The combined organic layers are washed with brine and dried over anhydrous sodium sulfate. The solution is concentrated under reduced pressure and the residue purified by preparative TLC on silica gel to afford 6,8a-deepoxy-6,8a-dihydroxyavermectin $B_{2a}/B_{2b}$.

EXAMPLE 10

8a-Hydroxyavermectin A1a/A1b

To a solution of anhydrous avermectin $A_{1a}/A_{1b}$ (360 mg) in 6 ml of dry benzene, 1 mg of copper (I) chloride and 0.085 ml of tert-butyl peroxybenzoate is added under a blanket of nitrogen. The reaction mixture is placed in a preheated oil bath at 95° C. and stirred at reflux for 12 hours. The mixture was then added to an ethyl acetate/5% sodium bicarbonate solution and the layers separated. The organic solution is back-washed with brine and concentrated to dryness. The residue is dissolved in 20 ml of 80/20 acetic acid/water and the mixture stirred at room temperature overnight. The reaction mixture is evaporated and the residue redissolved in ethyl acetate. This solution is washed with 5% sodium bicarbonate solution and brine before it is dried over anhydrous sodium sulfate. Concentration of this solution affords crude material which upon purification via preparative TLC on silica gel and preparative HPLC on a reverse-phase column gives 8a-hydroxyavermectin $A_{1a}/A_{1b}$.

EXAMPLE 11

6,8a-Deepoxy-6,8a-dihydroxyavermectin A1a/A1b

A solution of sodium borohydride (2.5 mg) in 0.3 ml of ethanol is added to a cold ($-5°$ C.) solution of 8a-hydroxyavermectin $A_{1a}/A_{1b}$ (11 mg) and $CeCl_3.7H_2O$ (4.5 mg) in 1 ml of ethanol. The reaction mixture is stirred for 3 hours at $-5°$ C. and then partitioned between ethyl acetate and 5% sodium bicarbonate solution. The layers are separated and the aqueous layer further extracted with ethyl acetate. The combined organic layers are back-washed with brine and dried over anhydrous sodium sulfate. The organic solution is concentrated under reduced pressure and the crude product purified by preparative TLC on silica gel to give 6,8a-deepoxy-6,8a-dihydroxyavermectin $A_{1a}/A_{1b}$.

EXAMPLE 12

8a-Hydroxyavermectin B1a/B1b monosaccharide

To a solution of anhydrous 5-O-(tert-butyldimethylsilyl)avermectin $B_{1a}/B_{1b}$ monosaccharide (600 mg) in 10 ml of dry benzene, 0.162 ml of tert-butyl peroxybenzoate and 1 mg of copper (I) chloride is added under nitrogen. The reaction mixture is placed in a preheated oil bath (95° C.) and then stirred at reflux for 12 hours. The mixture is added to an ethyl acetate/5% sodium bicarbonate solution and the resulting layers separated. The organic phase is washed with brine and then evaporated to dryness. The residue is redissolved in 40 ml of 80/20 acetic acid/water and stirred at room temperature for 24 hours. The reaction mixture is concentrated and the residue partitioned between ethyl acetate and 5% sodium bicarbonate solution. The ethyl acetate phase is washed with brine and then dried over anhydrous sodium sulfate. Concentration affords crude product which is purified by preparative TLC on silica gel and preparative HPLC on a reverse-phase column to give 8a-hydroxyavermectin $B_{1a}/B_{1b}$ monosaccharide.

EXAMPLE 13

6,8a-Deepoxy-6,8a-dihydroxyavermectin B1a/B1b monosaccharide

A solution of 21 mg of 8a-hydroxyavermectin $B_{1a}/B_{1b}$ monosaccharide and 12 mg of $CeCl_3.7H_2O$ in 1.5 ml of ethanol at $-5°$ C. is treated with an ethanolic solution of sodium borohydride (1.6 mg in 0.2 ml). The reaction mixture is stirred at $-5°$ C. for 1.5 hours and then partitioned between ethyl acetate and 5% sodium bicarbonate solution. The layers are separated and the aqueous layer further extracted with ethyl acetate. The combined organic layers are back-washed with brine and then dried over anhydrous magnesium sulfate. Evaporation affords crude product which can be purified by preparative TLC to give 6,8a-Deepoxy-6,8a-dihydroxyavermectin $B_{1a}/B_{1b}$ monosaccharide.

EXAMPLE 14

8a-Hydroxy-22,23-dihydroavermectin B1a/B1b aglycone

A solution of 380 mg of anhydrous 5-O-(tert-butyldimethylsilyl)avermectin $B_{1a}/B_{1b}$ aglycone and 2 mg of copper (I) chloride in 7.5 ml of dry benzene is treated with 0.13 ml of tert-butyl peroxybenzoate under nitrogen. The reaction mixture is placed in a preheated oil bath at 95° C. and the mixture stirred at reflux for 12 hours at which point it is partitioned between ethyl acetate and 5% sodium bicarbonate solution. The layers are separated and the aqueous phase further extracted with ethyl acetate. The combined organic layers are back-washed with brine and evaporated to dryness. The residue is redissolved in 30 ml of 80/20 acetic acid/water and stirred at room temperature for 24 hours. The reaction mixture is concentrated and the residue dissolved in ethyl acetate and washed with 5% sodium bicarbonate solution and brine. The organic solution is dried over anhydrous sodium sulfate and concentrated to give crude product. Purification of this material via preparative TLC on silica gel and preparative HPLC on a reverse-phase column affords 8a-hydroxy-22,23-dihydroavermectin $B_{1a}/B_{1b}$ aglycone.

EXAMPLE 15

6,8a-Deepoxy-6,8a-dihydroxy-22,23-dihydroavermectin B1a/B1b aglycone

To a solution of 8a-hydroxy-22,23-dihydroavermectin $B_{1a}/B_{1b}$ aglycone (18.5 mg) and $CeCl_3.7H_2O$ (12 mg) in 1.5 ml of ethanol at $-5°$ C., an ethanolic solution of sodium borohydride (1.7 mg in 0.2 ml) is added. The reaction mixture is stirred at room temperature for 1.5 hours at $-5°$ C. and then partitioned between ethyl acetate and 5% sodium bicarbonate solution. The layers are separated and the aqueous layer further extracted with ethyl acetate. The combined organic layers are back-washed with brine and dried over anhydrous magnesium sulfate. Evaporation of this solution gives crude product which upon purification on silica gel affords 6,8a-deepoxy-6,8a-dihydroxy-22,23-dihydroavermectin $B_{1a}/B_{1b}$ aglycone.

EXAMPLE 16

8a-Hydroxy-13-deoxy-22,23-dihydroavermectin $B_{1a}$ aglycone

To a solution of anhydrous 5-O-(tert-butyldimethylsilyl)-13-deoxy-22,23-dihydroavermectin $B_{1a}$ aglycone (460 mg) in 10 ml of dry benzene, 1 mg of copper (I) chloride and 0.16 ml of tert-butyl peroxybenzoate is added under nitrogen. The reaction mixture is placed in a preheated oil bath at 95° C. and stirred at reflux for 12 hours. The mixture is then added to an ethyl acetate/5% sodium bicarbonate solution and the layers separated. The organic solution is back-washed with brine and concentrated to dryness. The residue is dissolved in 30 ml of 80/20 acetic acid/water and the mixture stirred at room temperature overnight. The reaction mixture is concentrated and the residue dissolved in ethyl acetate. This solution is washed with 5% sodium bicarbonate solution and brine before it is dried over anhydrous magnesium sulfate. Concentration of this solution affords crude material which upon purification by preparative TLC on silica gel and preparative HPLC (reverse-phase column) gives 8a-hydroxy-13-deoxy-22,23-dihydroavermectin $B_{1a}$ aglycone.

EXAMPLE 17

6,8a-Deepoxy-6,8a-dihydroxy-13-deoxy-22,23-dihydroavermectin $B_{1a}$ aglycone

A solution of sodium borohydride (1.6 mg) in 0.2 ml of ethanol is added to a cold ($-5°$ C.) solution of 8a-hydroxy-13-deoxy-22,23-dihydroavermectin $B_{1a}$ aglycone (16 mg) and CeCl$_3$·7H$_2$O (12 mg) in 1.5 ml of ethanol. The reaction mixture is stirred for 2 hours at −5° C. and then partitioned between ethyl acetate and 5% sodium bicarbonate solution. The layers are separated and the aqueous layer further extracted with ethyl acetate. The combined organic layers are back-washed with brine and dried over anhydrous sodium sulfate. The organic solution is concentrated under reduced pressure and the crude product purified by preparative TLC on silica gel to give 6,8a-deepoxy-6,8a-dihydroxy-13-deoxy-22,23-dihydroavermectin B$_{1a}$ aglycone.

EXAMPLE 18

8a-Hydroxy-13-deoxy-22,23-dihydroavermectin B1b aglycone

To a solution of anhydrous 5-O-)tert-buryl-dimethylsilyl)-13-deoxy-22,23-dihydroavermectin B$_{1b}$ aglycone (230 mg) in 5 ml of dry benzene, 0.082 ml of tert-butyl peroxybenzoate and 1 mg of copper (I) chloride is added under nitrogen. The reaction mixture is placed in a preheated oil bath (95°C.) and then stirred at reflux for 12 hours. The mixture is added to an ethyl acetate/5% sodium bicarbonate solution and the resulting layers separated. The organic phase is washed with brine and then evaporated to dryness. The residue is redissolved in 20 ml of 80/20 acetic acid/water and stirred at room temperature for 24 hours. The reaction mixture is concentrated and the residue distributed between ethyl acetate and 5% sodium bicarbonate solution. The ethyl acetate phase is washed with brine and then dried over anhydrous sodium sulfate. Concentration affords crude product which is purified by preparative TLC on silica gel and preparative HPLC on reverse-phase column to give 8a-hydroxy-13deoxy-22,23-dihydroavermectin B$_{1b}$ aglycone.

EXAMPLE 19

6,8a-Deepoxy-6,8a-dihydroxy-13-deoxy-22,23-dihydroavermectin B1b aglycone

A solution of 32 mg of 8a-hydroxy-13-deoxy-22,23-dihydroavermectin B$_{1b}$ aglycone and 24 mg of CeCl$_3$·7H$_2$O in 3.0 ml of ethanol at −5° C. is treated with an ethanolic solution of sodium borohydride (3.2 mg in 0.3 ml). The reaction mixture is stirred at −5° C. for 1.5 hours and then partitioned between ethyl acetate and 5% sodium bicarbonate solution. The layers are separated and the aqueous layer further extracted with ethyl acetate. The combined organic layers are back-washed with brine and then dried over anhydrous sodium sulfate. Evaporation affords crude product which can be purified by preparative TLC to give 6,8a-deepoxy-6,8a-dihydroxy-13-deoxy-22,23-dihydroavermectin B$_{1b}$ aglycone.

EXAMPLE 20

8a-Hydroxy-milbemycin $\alpha_1/\alpha_3$

A solution of 460 mg of anhydrous 5-O-(tert-butyldimethylsilyl) milbemycin $\alpha_1/\alpha_3$ and 1 mg of copper (I) chloride in 10 ml of dry benzene is treated with 0.18 ml of tert-butyl peroxybenzoate under nitrogen. The reaction mixture is placed in a preheated oil bath at 95° C. and the mixture stirred at reflux for 12 hours at which point it is partitioned between ethyl acetate and 5% sodium bicarbonate solution. The layers are separated and the aqueous phase further extracted with ethyl acetate. The combined organic layers are back-washed with brine and evaporated to dryness. The residue is dissolved in 40 ml of 80/20 acetic acid/water and permitted to stir at room temperature overnight. The reaction mixture is taken to dryness under vacuum and the resulting residue redissolved in ethyl acetate. This solution is washed with 5% sodium bicarbonate solution and brine and then dried over anhydrous sodium sulfate. Concentration of this solution gives crude product. Purification of this material by preparation TLC on silica gel followed by preparative HPLC on a reverse-phase column affords 8a-hydroxy-milbemycin $\alpha_1/\alpha_3$.

EXAMPLE 21

6,8a-Deepoxy-6,8a-dihydroxy-milbemycin $\alpha_1/\alpha_3$

To a solution of 8a-hydroxy-milbemycin $\alpha_1/\alpha_3$ (15.5 mg) and CeCl$_3$·7H$_2$O (12 mg) in 1.5 ml of ethanol at −5° C., an ethanolic solution of sodium borohydride (1.7 mg in 0.2 ml) is added. The reaction mixture is stirred for 1.5 hours at −5° C. and then partitioned between ethyl acetate and 5% sodium bicarbonate solution. The layers are separated and the aqueous layer further extracted with ethyl acetate. The combined organic layers are back-washed with brine and dried over anhydrous magnesium sulfate. Evaporation of this solution gives crude product which upon purification on silica gel affords 6,8a-deepoxy-6,8a-dihydroxy-milbemycin $\alpha_1/\alpha_3$.

EXAMPLE 22

4''-Methylamino-4''-deoxy-8a-hydroxy-22,23-dihydroavermectin B1a/B1b

To a solution of anhydrous 5-O-(tert-butyl-dimethylsilyl)-4''-methylamino-4''-deoxy-22,23-dihydroavermectin B1a/B1b hydrochloride (370 mg) and 1 mg of copper (I) chloride in 5 ml of anhydrous benzene is added 1.2 ml of tert-butyl peroxybenzoate. The mixture is then placed in a preheated oil bath at 95° C. and the reaction mixture stirred at reflux for 12 hours. The reaction mixture is mixed with 5% sodium bicarbonate solution and diluted with ethyl acetate. The layers are separated and the organic phase back-washed with brine and then concentrated under reduced pressure. The residue is treated with 20 ml of 80/20 acetic acid/water and stirred at room temperature for 24 hours. The reaction mixture is evaporated and the residue dissolved in ethyl acetate. The solution is washed with 5% sodium bicarbonate solution and brine. The mixture is dried over anhydrous sodium sulfate and concentrated to afford crude product which is used in the next reaction without purification.

EXAMPLE 23

4''-Methylamino-4''-deoxy-6,8a-deepoxy-6,8a-dihydroxy-22,23-dihydroavermectin B1a/B1b The crude product (150 mg) from Example 22 and CeCl$_3$·7H$_2$O (75 mg) are dissolved in 10 ml of absolute ethanol and cooled to −5° C. To this mixture a solution of sodium borohydride (10 mg) in 1 ml of ethanol is slowly added and the resulting mixture stirred at −5° C. for 4 hours. The reaction mixture is then poured into a mixture of ethyl acetate and 5% sodium bicarbonate solution. The layers are separated and the aqueous phase further extracted with ethyl acetate. The combined organic extracts are back-washed with brine and dried over anhydrous magnesium sulfate. Concentration affords the crude product which is purified by preparative TLC on silica gel and preparative HPLC on a reverse phase column to give 4"-methylamino-4"-deoxy-6,8a-deepoxy-6,8a-dihydroxy-22,23-dihydroavermectin B1a/B1b.

EXAMPLE 24

8a-O-Acetyl-6,8a-deepoxy-6,8a-dihydroxyavermectin B1a

A solution of 100 mg of 6,8a-deepoxy-6,8a-dihydroxyavermectin B1a (Example 2) in 10 ml of anhydrous ethyl acetate is stirred under a nitrogen atmosphere at 60° C. in the presence of 1 g of neutral alumina. The reaction is monitored by TLC. At the appropriate time the reaction mixture is filtered and the solid alumina is thoroughly washed with ethyl acetate. The combined filtrate is washed with 5% sodium bicarbonate solution and then conentrated to dryness under reduced pressure. The residue is purified by preparative TLC to give the desired monoacetate derivative.

EXAMPLE 25

4",5,6,8a-Tetra-O-acetyl-6,8a-deepoxy-6,8a-dihydroxyavermectin B1a/B1b

A solution of 6,8a-deepoxy-6,8a-dihydroxyavermectin B1a/B1b (50 mg) in 1 ml of anhydrous pyridine is stirred rapidly at 0° C. while 0.5 ml of acetic anhydride is added slowly. The cold mixture is then stirred for 6 hours before pouring into ice-water. Ethyl acetate is added and the layers mixed. The layers are separated and the aqueous layer further extracted with ethyl acetate. The combined organic layers are washed with 5% sodium bicarbonate solution and water and then dried with anhydrous sodium sulfate. The solution is concentrated and the residue purified by preparative TLC to give the titled compound.

EXAMPLE 26

4",5-Di-O-acetyl-8a-hydroxy-22,23-dihydroavermectin B1a/B1b

Tert-butyl peroxybenzoate (0.82 ml) is added to a solution of 300 mg of anhydrous 4",5-di-O-acetyl-22,23-dihydroavemectin B1a/B1b and 0.5 mg of copper (I) chloride in 5 ml of anhydrous benzene under nitrogen. The reaction mixture is placed in a preheated oil bath at 95° C. and the mixture stirred at reflux for 12 hours. The reaction mixture is added to 5% sodium bicarbonate solution and diluted with ethyl acetate. The layers are separated and the organic phase back-washed with brine and then concentrated. The residue is treated with 20 ml of 80/20 acetic acid/water and stirred at room temperature for 24 hours. The reaction mixture is concentrated under reduced pressure and the residue dissolved in ethyl acetate. The solution is washed with 5% sodiun bicarbonate solution and brine and then dried with anhydrous sodium sulfate. Concentration affords the crude product which is purified by preparative TLC on silica gel and then preparative HPLC on a reverse-phase column to give pure 4",5-di-O-acetyl-8a-hydroxy-22,23-dihydroavermectin B1a/B1b.

EXAMPLE 27

4",5-Di-O-acetyl-6,8a-deepoxy-6,8a-dihydroxy-22,23-dihydroavermectin B1a/B1b

To a solution of 4",5-di-O-acetyl-8a-hydroxy-22,23-dihydroavermectin B1a/B1b (25 mg) and $CeCl_3 \cdot 7H_2O$ (12 mg) in 2 ml of ethanol at $-5°$ C., a solution of sodium borohydride (3mg in 0.4 ml of ethanol) is added. The reaction mixture is stirred at $-5°$ C. for 2 hours and then poured into a mixture of ethyl acetate and 5% sodium bicarbonate solution. The layers are separated and the aqueous phase further extracted with ethyl acetate. The combined organic extracts are back-washed with brine and dried over anhydrous magnesium sulfate. Evaporation of this solution affords crude product which when purified by preparative TLC gives 4",5-di-O-acetyl-6,8a-deepoxy-6,8a-dihydroxy-22,23-dihydroavermectin B1a/B1b.

EXAMPLE 28

6,8a-deepoxy-6,8a-22,23-dihydroavermectin B1a/B1b-8,9-oxide

To a solution of 120 mg of 6,8a-deepoxy-6,8a-dihydroxy-22,23-dihydroavermectin B1a/B1b (Example 7) and 5 mg of vanadyl acetyl acetonate in 10 ml of benzene, 25 mg of 70% tert-butyl hydroperoxide is slowly added at room temperature. The reaction mixture is stirred until judged to be complete by TLC. The reaction mixture is diluted with ethyl acetate and then mixed with an aqueous solution of sodium bisulfite. The layers are separated and the organic layer further washed with sodium bisulfite, sodium bicarbonate and brine. The organic solution is dried with anhydrous sodium sulfate and concentrated to dryness. The crude product is purified by preparative TLC on silica gel to give the 8,9-oxide(s).

What is claimed is:

1. A compound having the formula:

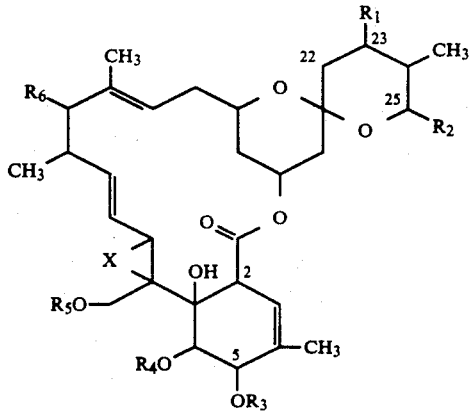

wherein the broken line at the 22,23-position indicates a single or double bond;

$R_1$ is H or hydroxy; the hydroxy being present only when said broken line indicates a single bond;

$R_2$ is methyl, ethyl, iso-propyl or sec-butyl $R_3$ is hydrogen, methyl or acetyl;

$R_4$ and $R_5$ are hydrogen or acetyl;

X is oxygen or a double bond;

$R_6$ is hydroxy,

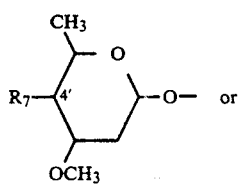

or

-continued

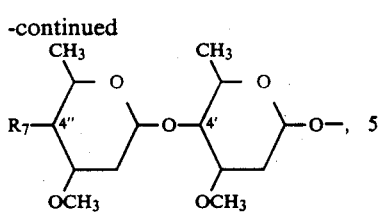

where $R_7$ is hydroxy, $NR_8R_9$, wherein $R_8$ and $R_9$ are independently hydrogen, loweralkyl, loweralkanoyl, loweralkyl sulfonyl or substituted benzenesulfonyl, wherein the substituent is halogen or $R_{10}COO-$, wherein $R_{10}$ is a loweralkyl, phenyl or loweralkyl substituted phenyl.

2. The compound of claim 1 which is 6,8a-Deepoxy-6,8a-dihydroxyavermectin B1a/B1b.

3. The compound of claim 1 which is 6,8a-Deepoxy-6,8a-22,23-dihydroavermectin B1a/B1b.

4. The compound of claim 1 which is 6,8a-Deepoxy-6,8a-dihydroxyavermectin B1a/B1b monosaccharide.

5. The compound of claim 1 which is 6,8a-Deepoxy-6,8a-dihydroxyavermectin B1a/B1b aglycone.

6. The compound of claim 1 which is 4"-Methylamino-4"-deoxy-6,8a-deepoxy-6,8a-dihydroxy-22,23-dihydroavermectin B1a/B1b.

7. The compound of claim 1 which is 6,8a-Deepoxy-6,8a-22,23-dihydroavermectin B1a aglycone.

8. The compound of claim 1 which is 4",5,6,8a-Tetra-O-acetyl-6,8a-deepoxy-6,8a-avermectin B1a/B1b.

9. The compound of claim 1 which is 6,8a-Deepoxy-6,8a-dihydroxy-22,23-dihydroavermectin B1a/B1b-8,9-oxide.

10. The compound of claim 1 which is 6,8a-Deepoxy-6,8a-13-deoxy-22,23-dihydroavermectin B1a/B1b aglycone.

11. The compound of claim 1 which is 6,8a-Deepoxy-6,8a-dihydroxy-13-deoxy-22,23-dihydroavermectin B1b aglycone.

12. A method for the treatment of parasitic infections which comprises administering to an animal infected with parasites an effective amount of a compound of claim 1.

13. A method for the treatment of insect infestations of plants which comprises treating such plants or the soil in which they grow with an effective amount of a compound of claim 1.

14. A composition useful for treating parasitic infections of animals and parasitic infestations of plants, plant products or soil which comprises an inert carrier and an effective amount of a compound of claim 1.

* * * * *